(12) United States Patent
Liu et al.

(10) Patent No.: US 10,297,417 B2
(45) Date of Patent: May 21, 2019

(54) METHOD FOR CHARACTERIZING TWO DIMENSIONAL NANOMATERIAL

(71) Applicants: Tsinghua University, Beijing (CN); HON HAI PRECISION INDUSTRY CO., LTD., New Taipei (TW)

(72) Inventors: Peng Liu, Beijing (CN); Wei Zhao, Beijing (CN); Xiao-Yang Lin, Beijing (CN); Duan-Liang Zhou, Beijing (CN); Chun-Hai Zhang, Beijing (CN); Kai-Li Jiang, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 115 days.

(21) Appl. No.: 15/615,310

(22) Filed: Jun. 6, 2017

(65) Prior Publication Data

US 2017/0358420 A1    Dec. 14, 2017

(30) Foreign Application Priority Data

Jun. 8, 2016 (CN) .......................... 2016 1 0405276

(51) Int. Cl.
*H01J 37/26* (2006.01)
*H01J 37/16* (2006.01)
*H01J 37/244* (2006.01)

(52) U.S. Cl.
CPC .............. *H01J 37/26* (2013.01); *H01J 37/16* (2013.01); *H01J 37/244* (2013.01);
(Continued)

(58) Field of Classification Search
CPC .......... H01J 37/26; H01J 37/16; H01J 37/244; H01J 2237/2602; H01J 2237/24585; H01J 2237/24455; H01J 2237/2443
(Continued)

(56) References Cited

U.S. PATENT DOCUMENTS 5,767,521 A * 6/1998 Takeno ................. B82Y 10/00
                                                      250/492.2
9,991,094 B2 * 6/2018 Liu .................. G01N 23/20058
(Continued)

FOREIGN PATENT DOCUMENTS

JP       19960139013 A     5/1996
JP       20040518277 A     6/2004
(Continued)

OTHER PUBLICATIONS

Marlene Adrian et al. "Complete analysis of a transmission electron diffraction pattern of a MoS2-graphite heterostructure", ULtrmicroscopy, vol. 166, p. 9-15, Apr. 9, 2016, http://dx.doi.org/10.1016/j.ultramic.2016.04.002.
(Continued)

*Primary Examiner* — Michael Maskell
(74) *Attorney, Agent, or Firm* — ScienBiziP, P.C.

(57) ABSTRACT

The disclosure relates to a method for characterizing a two-dimensional nanomaterial sample. The two-dimensional nanomaterial sample is placed in a vacuum chamber. An electron beam passes through the two-dimensional nanomaterial sample to form a diffraction electron beam and a transmission electron beam to form an image on an imaging device. An angle θ between the diffraction electron beam and the transmission electron is obtained. A lattice period d of the two-dimensional nanomaterial sample is calculated according to a formula $d \sin \theta \approx d\theta = \lambda$, where λ represents a wavelength of the electron beam.

19 Claims, 16 Drawing Sheets

(52) U.S. Cl.
CPC .............. *H01J 2237/2443* (2013.01); *H01J 2237/24455* (2013.01); *H01J 2237/24585* (2013.01); *H01J 2237/2602* (2013.01)

(58) Field of Classification Search
USPC ............................ 250/306, 307, 310, 311
See application file for complete search history.

(56) References Cited

U.S. PATENT DOCUMENTS

| | | | |
|---|---|---|---|
| 2003/0052342 A1 | 3/2003 | Kim | |
| 2004/0183012 A1* | 9/2004 | Yaguchi | G01N 23/20 250/306 |
| 2004/0209415 A1 | 10/2004 | Kim | |
| 2014/0124776 A1 | 5/2014 | Takahashi et al. | |
| 2015/0108351 A1* | 4/2015 | Ogashiwa | H01J 37/28 250/311 |
| 2015/0179396 A1* | 6/2015 | Yaguchi | H01J 37/20 250/310 |

FOREIGN PATENT DOCUMENTS

| | | |
|---|---|---|
| JP | 20100014548 A | 1/2010 |
| JP | 20130229267 A | 11/2013 |
| TW | 201430920 A | 8/2014 |
| TW | 201519279 A | 5/2015 |
| WO | 2013/129514 A1 | 9/2013 |
| WO | 2014185074 A1 | 11/2014 |

OTHER PUBLICATIONS

Max Guide et al., "Ultrafast low-energy electron diffraction in transmission resolves polymer/graphene superstructure dynamics", Science, vol. 345, No. 6193, p. 200-204, Jul. 11, 2014, http://dx.doi.org/10.1126/sicence.1250658.

Melanie Muller et al. "Femtosecond electrons probing currents and atomic structure in nanomaterials", Nature Communication, vol. 5, Oct. 31, 2014, http://doi.org/10.1038/ncomms6292.

* cited by examiner (a) 2D material  (b) 3D material

METHOD FOR CHARACTERIZING TWO DIMENSIONAL NANOMATERIAL

CROSS-REFERENCE TO RELATED APPLICATIONS

This application claims all benefits accruing under 35 U.S.C. § 119 from China Patent Application No. 201610405276.7, filed on Jun. 8, 2016 in the China Intellectual Property Office, the disclosure of which is incorporated herein by reference.

BACKGROUND

1. Technical Field

The present disclosure relates to a transmission-type low energy electron microscopy and a transmitted electron diffraction method to characterize the large area two-dimensional nanomaterial sample.

2. Description of Related Art

Graphene has attracted great interest owing to its unique properties and potential applications. A requirement for high-end applications of graphene, particularly in electronics and photonics, is the complete control over the structure of the material, i.e., lateral size, layer thickness homogeneity, and purity. Thus, wafer-scale single crystal graphene is highly sought in these years.

At present, single crystal graphene domains, from millimeter-sized to centimeter-sized, can be synthesized by CVD. The most accurate and decisive method to characterize the crystalline nature of a graphene domain is electron diffraction, such as low energy electron diffraction (LEED) and selected area electron diffraction (SAED). Usually, some sample points were selected uniformly in a specific area, and the LEED/SAED patterns at the points were collected. The crystal distribution is given by comparing these LEED/SAED patterns. LEED pattern comes from the backscattered electrons, which will include a signal from the substrate beneath the graphene. The small beam size of LEED also limits the characterization efficiency. SAED pattern in transmission electron microscope (TEM) comes from the transmitted electrons at high energy. Since large magnification and high resolution are required for the modern TEM development, the size of SAED aperture is usually from nanometer size to micrometer size. It is time-consuming to map the crystal distribution of one graphene domain at even millimeter size. Besides that, sample larger than 3 millimeters cannot be entirely transferred onto the TEM grid because the holder size is fixed. It is necessary to develop an efficient method to characterize the crystal distribution of large area sample.

What is needed, therefore, is a method for characterizing a two-dimensional nanomaterial sample that overcomes the problems as discussed above.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

Figure 1:
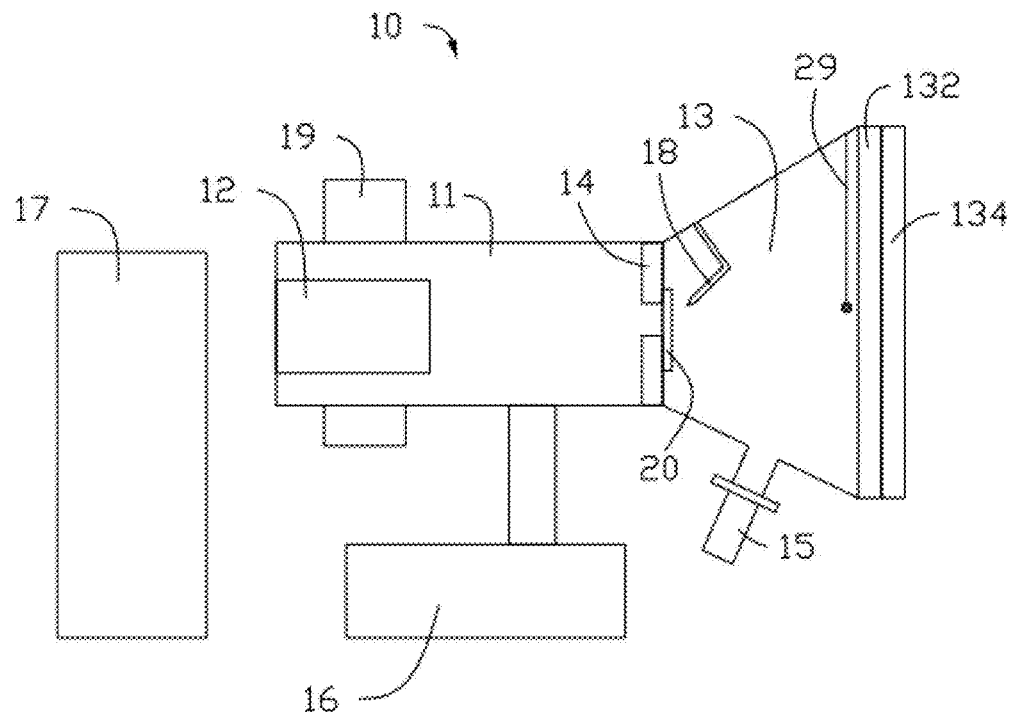
FIG. 1 is a schematic section view of one embodiment of a transmission-type low energy electron microscopy.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale, and the proportions of certain parts may be exaggerated to better illustrate details and features. The description is not to considered as limiting the scope of the embodiments described herein.

Several definitions that apply throughout this disclosure will now be presented.

The connection can be such that the objects are permanently connected or releasably connected. The term "substantially" is defined to essentially conforming to the particular dimension, shape or other word that substantially modifies, such that the component need not be exact. For example, substantially cylindrical means that the object resembles a cylinder, but can have one or more deviations from a true cylinder. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one. In general, the word "module," as used herein, refers to logic embodied in hardware or firmware, or to a collection of software instructions, written in a programming language, such as, for example, Java, C, or assembly. One or more software instructions in the modules may be embedded in firmware, such as an EPROM. It will be appreciated that modules may comprise connected logic units, such as gates and flip-flops, and may comprise programmable units, such as programmable gate arrays or processors. The modules described herein may be implemented as either software and/or hardware modules and may be stored in any type of computer-readable medium or other computer storage device.

References will now be made to the drawings to describe, in detail, various embodiments of the present transmission-type low energy electron microscopy and method for characterizing two-dimensional nanomaterial. This disclosure provides a transmitted electron diffraction method to characterize the centimeter-sized graphene domain at relatively low energy. The method has adopted an experimental scheme similar to that of Thomson which has demonstrated the wave nature of electrons. With a variable beam size from hundreds of micrometers to half a centimeter, transmitted electron diffraction and imaging of large area graphene sample can be easily observed to verify the crystal texture of large area sample. The relative crystal orientation in a different area is characterized in one test. The crystal distribution of polycrystalline $MoS_2$ has also been analyzed. With the low energy electron beam, a 2×2 0° adsorption pattern of water on suspended graphene is also observed.

Figure 2:
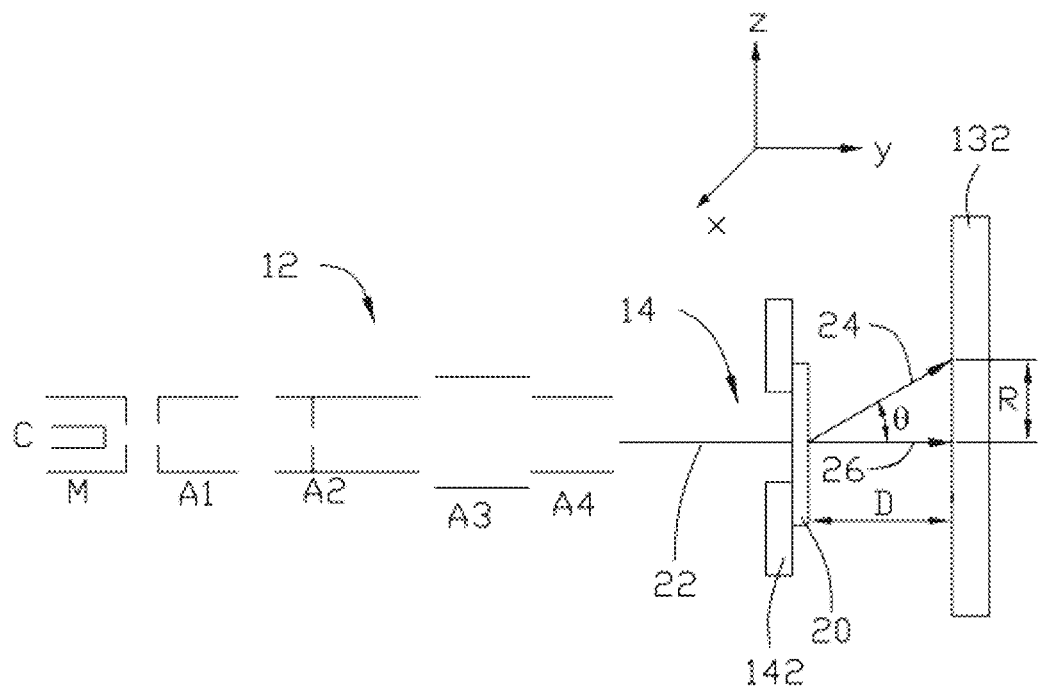
FIG. 2 is a schematic section view of electron diffraction and transmission of the transmission-type low energy electron microscopy.

Referring to FIGS. 1-2, a transmission-type low energy electron microscopy 10 of one embodiment is provided. The electron microscopy 10 comprises a vacuum chamber 11, an electron gun 12, a diffraction chamber 13, a sample holder 14, a core column 15, a vacuum pumping device 16, and a control computer 17.

The electron gun 12 is located in the vacuum chamber 11 and used to emit electron beam. The diffraction chamber 13 is in communication with the vacuum chamber 11. The sample holder 14 is used to fix a two-dimensional nanomaterial sample 20. The sample holder 14 can be located at the joint between the vacuum chamber 11 and the diffraction chamber 13. Thus, the electron beam emitted from the electron gun 12 can pass through the two-dimensional nanomaterial sample 20 and enter the diffraction chamber 13. The core column 15 is communicated to the diffraction chamber 13. The vacuum pumping device 16 is communicated to the vacuum chamber 11. The control computer 17 is used to control the work of the electron microscopy 10.

An imaging device 132 and an anode 134 is located in the diffraction chamber 13. The imaging device 132 is located between the electron gun 12 and the anode 134. The electron beam emitted from the electron gun 12 would move to the imaging device 132 under the force of anode 134. The electron beam emitted from the electron gun 12 would pass through the two-dimensional nanomaterial sample 20 and reach the imaging device 132 to form diffraction spot and/or diffraction imaging. The diffraction spot and/or diffraction imaging can be used to analysis the structure of the two-dimensional nanomaterial sample 20. The imaging device 132 can be a fluorescent screen configured to directly show the diffraction spot and/or diffraction imaging or a charge coupled device (CCD) to acquire and send the diffraction spot and/or diffraction imaging to the control computer 17.

The electron beam emitted from the electron gun 12 can have an energy in a range from about 800 eV to about 3000 eV, a current in a range from about 0.1 microampere to about 1 microampere, and a spot diameter in a range from about 100 micrometers to about 1 centimeter. The electron gun 12 can include a hot cathode electron source or a field emission cold cathode electron source. As shown in FIG. 2, in one embodiment, the electron gun 12 is a pre-focusing multiple lens beam electron gun using a quadrupole electrostatic focusing system. The electron gun 12 includes a cathode electron emitter C and four focusing electrodes A1, A2, A3, and A4. The four focusing electrodes are used to control the spot diameter of the electron beam. The electron gun 12 can also be a laminar gun. The laminar gun can have a more uniform spot and greater current density to improve the imaging diffraction quality. Furthermore, the electron microscopy 10 can include a moving platform 19 configured to move the electron gun 12 to scan the two-dimensional nanomaterial sample 20.

The sample holder 14 can have any structure and size as long as it can be used to fix the two-dimensional nanomaterial sample 20. In one embodiment, the sample holder 14 is a round copper plate having a round through hole in the middle of the plate. The diameter of the through hole is less than the size of the two-dimensional nanomaterial sample 20 so that the two-dimensional nanomaterial sample 20 can cover the through hole. The sample holder 14 can further include a moving device so that the two-dimensional nanomaterial sample 20 can be moved along XYZ directions and scanned by the electron beam.

The sample holder 14 can further include a heating element to heat the two-dimensional nanomaterial sample 20. Thus, the structure and interaction of the two-dimensional nanomaterial sample 20 under various temperature can be observed. The sample holder 14 can be heated to a temperature in a range from room temperature to about 1500K. In one embodiment, sample holder 14 includes tow electrodes 142 spaced from each other. The two-dimensional nanomaterial sample 20 is fixed on a supporter such as a copper mesh or a carbon nanotube film. Then, the supporter is fixed on and electrically connected to the two electrodes 142. The tow electrodes 142 can be used to apply a current to the supporter to heat the two-dimensional nanomaterial sample 20. The sample holder 14 can further include a temperature sensor to detect the temperature of the two-dimensional nanomaterial sample 20.

Furthermore, the electron microscopy 10 can include a sprayer 18. The sprayer 18 is adjacent to the sample holder 14 so that the material spray out of the sprayer 18 can be attached to the two-dimensional nanomaterial sample 20. Thus, the absorption or reaction between the two-dimensional nanomaterial sample 20 and other materials can be observed.

Furthermore, the electron microscopy 10 can include a conductive rod 29 having a first end and a second end opposite to the first end. The first end of the conductive rod 29 is fixed on the inner wall of the diffraction chamber 13. The conductive rod 29 is rotatable and can be rotated to be in front of the imaging device 132 to shield the zero-order diffraction spot or transmission spot. Thus, only diffraction image can be obtained by the imaging device 132. The electron microscopy 10 can also include a Faraday cup (not shown) so that only a single diffraction beam can be obtained from the imaging device 132.

Figure 3:
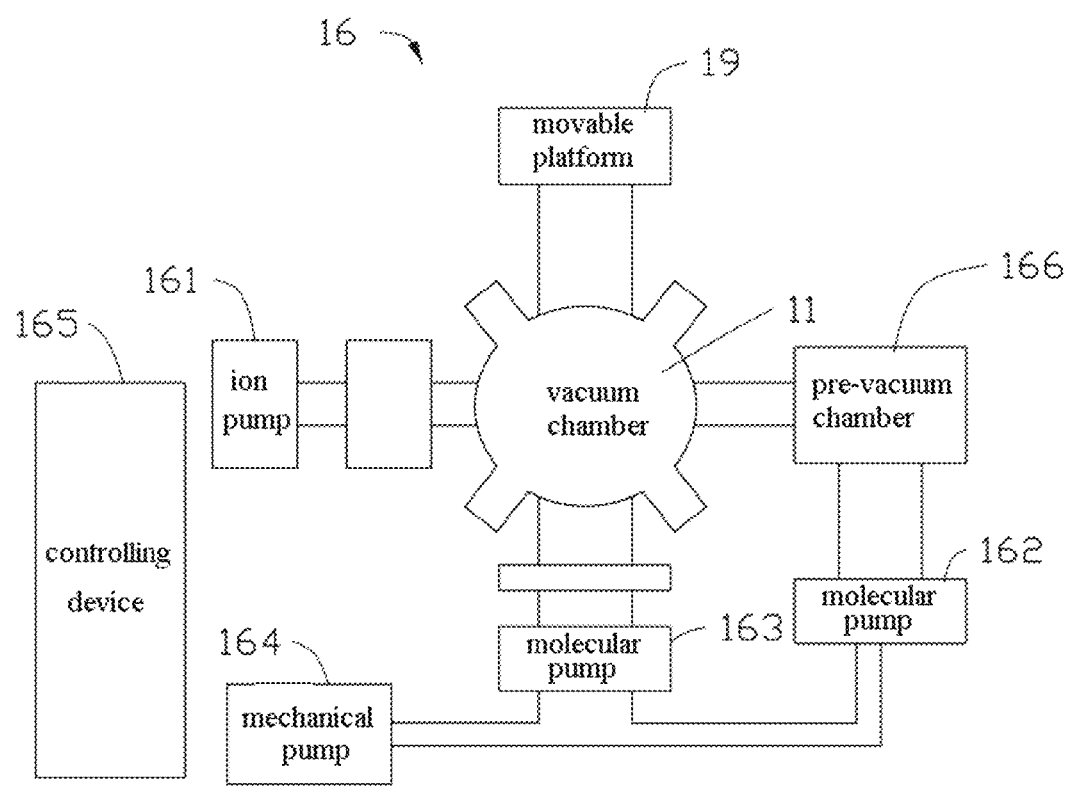
FIG. 3 is a schematic section view of one embodiment of a vacuum pumping device of the transmission-type low energy electron microscopy.

Referring to FIG. 3, the vacuum pumping device 16 of one embodiment includes an ion pump 161, a first molecular pump 162, a second molecular pump 163, a mechanical pump 164, and a control unit 165. The ion pump 161 and the second molecular pump 163 are respectively connected to the vacuum chamber 11. The first molecular pump 162 is connected to the vacuum chamber 11 via a pre-vacuum chamber 166. The mechanical pump 164 is respectively connected to the first molecular pump 162 and the second molecular pump 163. The control unit 165 is configured to control the work of the vacuum pumping device 16. The pressure of the vacuum chamber 11 can be kept at a range from about $10^{-3}$ Pa to about $10^{-6}$ Pa. The diffraction spots and diffraction image of transmission electron can be observed in the pressure range.

The control computer 17 includes a switching module, a calculating module, an image processing module, and a distance controlling module. The switching module is configured to switch the work of the electron microscopy 10 between large beam spot diffraction imaging mode and small beam spot diffraction imaging mode. In the large beam spot imaging mode, the electron beam is larger than the two-dimensional nanomaterial sample 20 and used to irradiate the entire surface of the two-dimensional nanomaterial sample 20 so that the diffraction imaging of the entire two-dimensional nanomaterial sample 20 is obtained. In the small beam spot imaging mode, the electron beam is smaller than the two-dimensional nanomaterial sample 20 and used to irradiate partial surface or scan the entire surface of the two-dimensional nanomaterial sample 20 so that the diffraction imaging of part of the two-dimensional nanomaterial sample 20 is obtained. The calculating module is configured to calculate the lattice period of the two-dimensional nanomaterial sample 20 as described below. The image processing module is configured to process the diffraction imaging, such as obtain radius R of diffraction ring. The distance controlling module is configured to adjust the distance D between the two-dimensional nanomaterial sample 20 and the imaging device 132.

The electron microscopy 10 is beneficial for two-dimensional nanomaterial, especially, two-dimensional nanomaterial only having a single layer of atoms. The difference between the conventional electron diffraction of three-dimensional nanomaterial and the electron diffraction of two-dimensional nanomaterial is described below.

Figure 4:
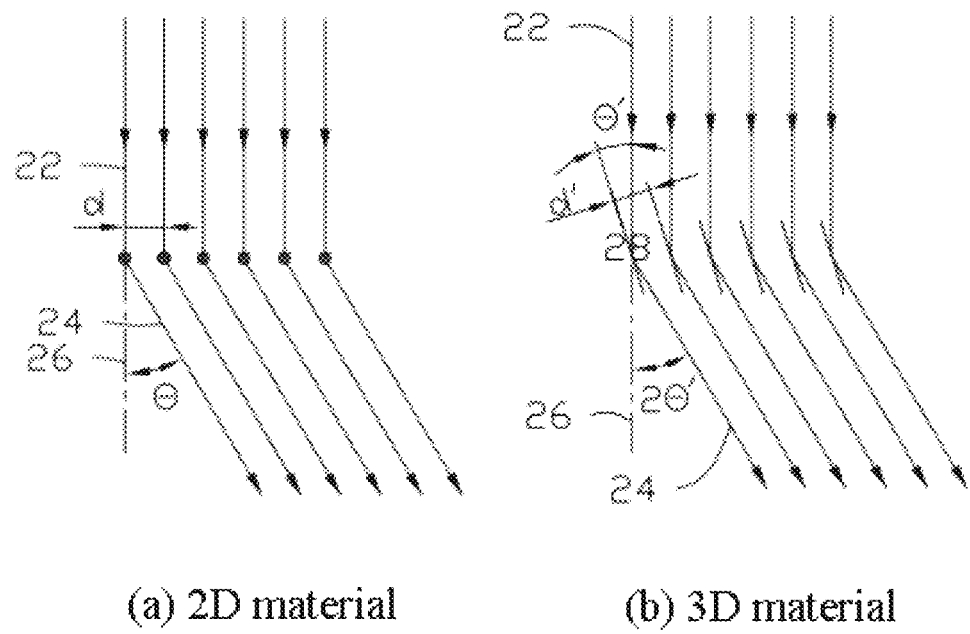
FIG. 4 is a schematic diagram of electron diffraction when electron beam passes through two-dimensional (2D) nanomaterial or three-dimensional (3D) nanomaterial.

Referring to FIG. 4(a), the electron diffraction of the two-dimensional nanomaterial satisfies the condition d sin $\theta=\lambda$, wherein d represents the lattice period of the two-dimensional nanomaterial, $\theta$ represents the angle between the diffraction electron beam 24 and the transmission electron beam 26. Referring to FIG. 4(b), the electron diffraction of the three-dimensional nanomaterial satisfies the condition 2d' sin $\theta'=\lambda$, wherein d' represents the interplanar spacing of the three-dimensional nanomaterial, $\theta'$ represents the angle between the incident electron beam 22 and the crystal surface 28 of the three-dimensional nanomaterial. In the conventional electron diffraction of three-dimensional nanomaterial, the angle between the diffraction electron beam 24 and the transmission electron beam 26 is $2\theta'$. Usually, in selected area electron diffraction, the $\theta$ or $\theta'$ is much small and satisfies the condition $\theta \cong \sin\theta \cong \tan\theta$ or $\theta' \cong \sin\theta' \cong \tan\theta'$. Thus, in the electron diffraction of the two-dimensional nanomaterial, it satisfies the condition d sin $\theta \cong d\theta=\lambda$, however, in the conventional electron diffraction of three-dimensional nanomaterial, it satisfies the condition 2d' sin $\theta' \cong 2d'\theta'=d'2\theta'=\lambda$.

The calculating module of the control computer 17 is configured to calculate the lattice period d of the two-dimensional nanomaterial sample 20 according to the formula d sin $\theta \cong d\theta=\lambda$. Referring to FIG. 2, along the same crystal direction, the diffraction electron beam 24 form a diffraction ring on the imaging device 132, and the transmission electron beam 26 form a transmission spot on the imaging device 132. The distance between the diffraction ring and the transmission spot is equal to the n radius R of diffraction ring and can be obtained by the distance controlling module of the control computer 17. The distance D between the two-dimensional nanomaterial sample 20 and the imaging device 132 can be obtained by the distance controlling module. The $\theta$ can be calculated by the radius R and distance D. The wavelength $\lambda$ can be obtained from the energy of the incident electron beam 22. Thus, the lattice period d of the two-dimensional nanomaterial sample 20 can be calculated according to the formula d sin $\theta \cong d\theta=\lambda$.

In both selected area electron diffraction and micro-diffraction, the transmission-type electron microscopy uses parallel or nearly parallel electron beam. In selected area electron diffraction, the diameter of the electron beam is in a range from about 0.5 micrometers to about 1 micrometer. In micro-diffraction, the diameter of the electron beam is less than 0.5 micrometers. In conventional electron diffractometer, electron beam smaller than the sample is used, and only parts of the sample are diffracted. LEED can have low energy electron microscopy (LEEM) mode, but the LEEM mode can only select one diffraction beam to form an image. The transmission-type electron microscopy 10 can be used to observe the two-dimensional nanomaterial sample 20 such as a single layer graphene, multi-layers graphene or $MoS_2$. The two-dimensional nanomaterial sample 20 can have a size in a range from about 10 micrometers to about several millimeters can be observed entirely. The two-dimensional nanomaterial sample 20 can have a size greater than 1 centimeter can be rapidly scanned by moving the two-dimensional nanomaterial sample 20. The energy of the electron beam of the transmission-type electron microscopy 10 is lower and would not destroy the two-dimensional nanomaterial sample 20. The two-dimensional nanomaterial sample 20 can be suspended by the sample holder 14 and prevented from being affected by the substrate. The examples of observing the graphene or $MoS_2$ using the transmission-type electron microscopy 10 are provided below.

Example 1

Figure 5:
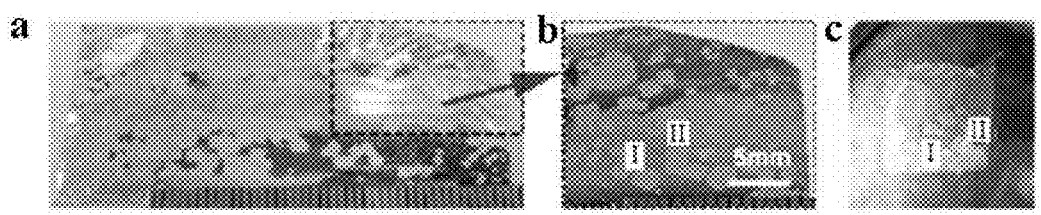
FIG. 5 shows optical images of graphene island sample of example 1.

Referring to FIGS. 5a-5b, in example 1, the two-dimensional nanomaterial sample 20 is graphene islands grown on a copper foil. FIG. 5a and FIG. 5b show graphene island grown on a copper foil by CVD method, and FIG. 5c shows a CGF(CNT/graphene hybrid film) including graphene islands located on crossed and stacked carbon nanotube films. Two graphene islands having an area greater than 1 square millimeters are marked respectively as numbers I and II. Referring to FIG. 5c, the two graphene islands respectively marked as numbers I and II are transferred from the copper foil to two layers of cross-stacking super-aligned drawn carbon nanotube film to form a CGF. The drawn carbon nanotube film includes a plurality of carbon nanotubes orderly arranged and spaced from each other. Thus, parts of the two graphene islands are suspended on a hole between adjacent carbon nanotubes. The drawn carbon nanotube film having the two graphene islands thereon is located on the round copper plate and covers the round through hole of the round copper plate. The drawn carbon nanotube film is an ultra thin, sparse porous structure and has little effect on the two-dimensional nanomaterial sample 20. Furthermore, because the primary diffraction spot of the drawn carbon nanotube film happens between adjacent wall of the carbon nanotubes, has a low angle and would not influence the diffraction spots of the two-dimensional nanomaterial sample 20.

Figure 6:
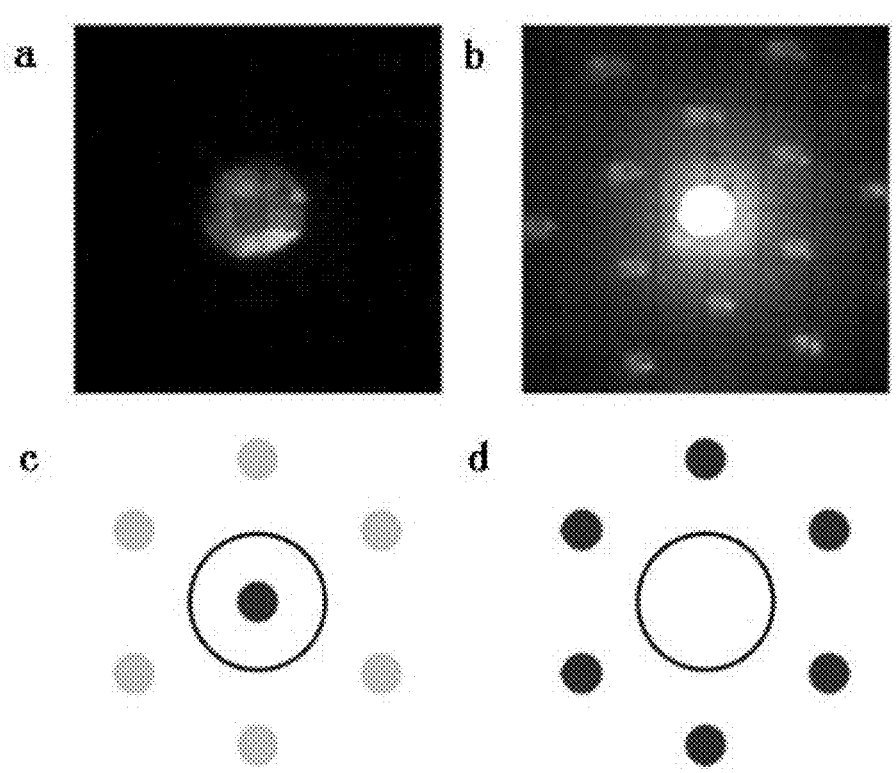
FIG. 6 shows transmission and diffraction images when electron beam passes through a graphene island I of FIG. 5 and schematic illustrations of transmission and diffraction images.

The two graphene islands are observed by the transmission-type electron microscopy 10. When the electron beam irradiates entire graphene island I, the central transmission image and diffraction image of graphene island I can be observed as shown in FIGS. 6a and 6b, respectively. As can be seen from FIGS. 6a and 6b, the shape of the transmission pattern and diffraction pattern correspond to that of graphene island I. FIGS. 6c and 6d show the schematics of transmission image and diffraction image for a single crystal graphene domain, respectively, which can illustrate FIGS. 6a and 6b well. Thus, the graphene island I is single layer graphene.

Figure 7:
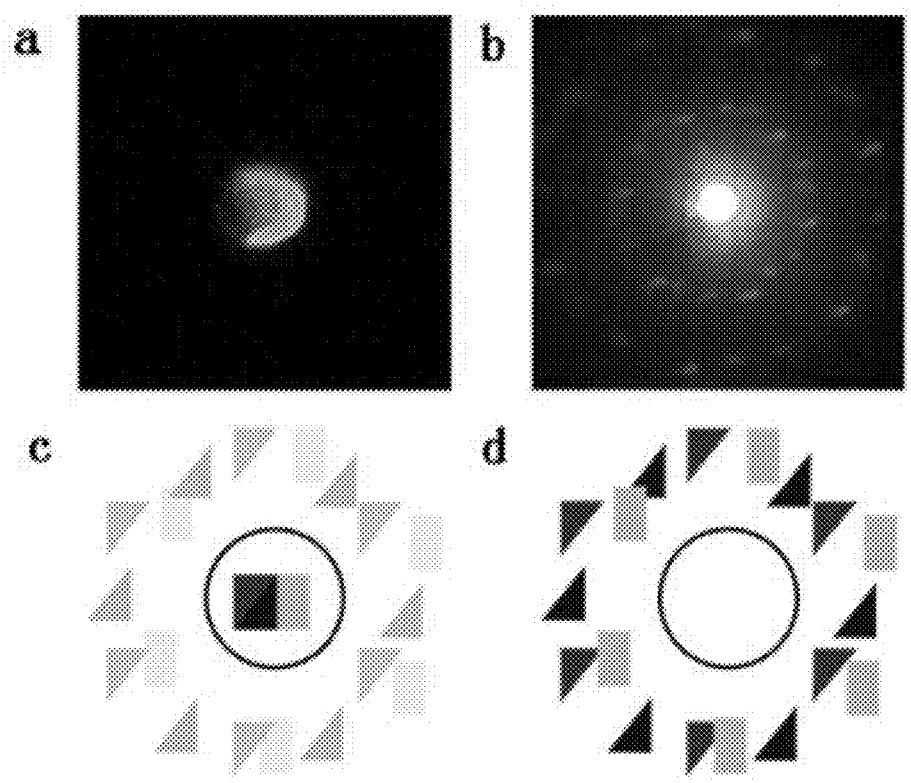
FIG. 7 shows transmission and diffraction images when electron beam passes through a graphene island II of FIG. 5 and schematic illustrations of transmission and diffraction images.

When the electron beam covers the whole graphene island II, the transmission image of graphene island II can be observed as shown in FIG. 7a similar to FIG. 6a but the diffraction image becomes a complex pattern as shown in FIG. 7b. FIGS. 7c and 7d show the schematics of transmission image and diffraction image for a graphene island including three single crystal graphene domains, helping us to understand FIG. 7b. Thus, the graphene island II includes three layer graphenes.

Figure 8:
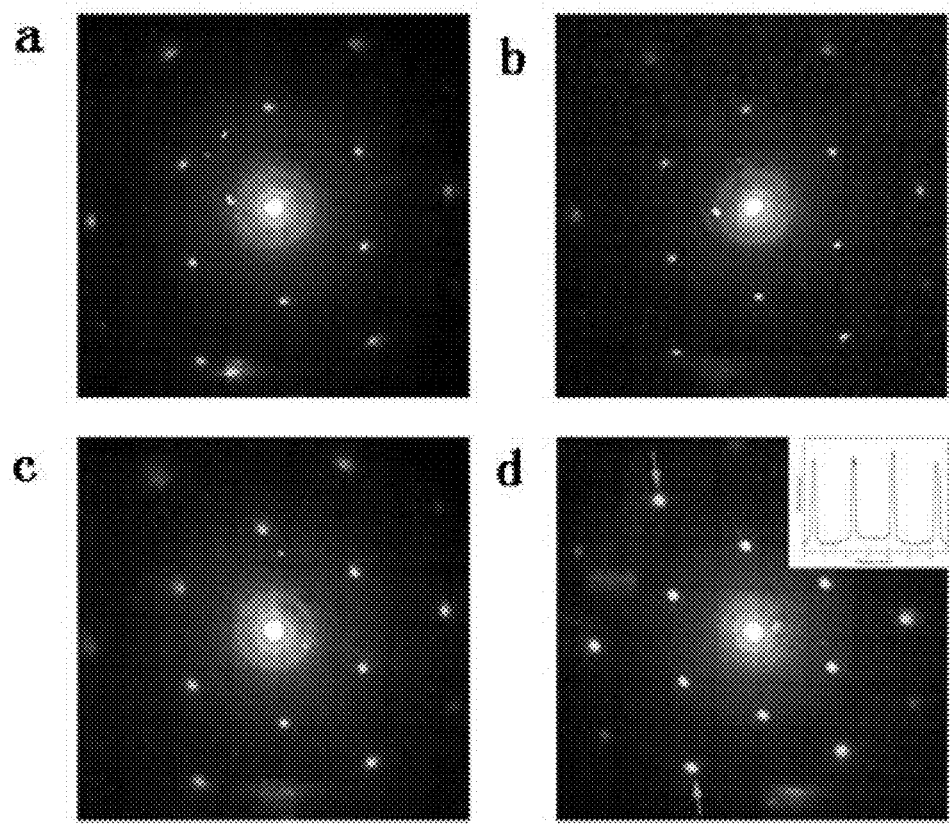
FIG. 8 shows electron diffraction patterns corresponding to four different regions in graphene island I of FIG. 5.
Figure 9:
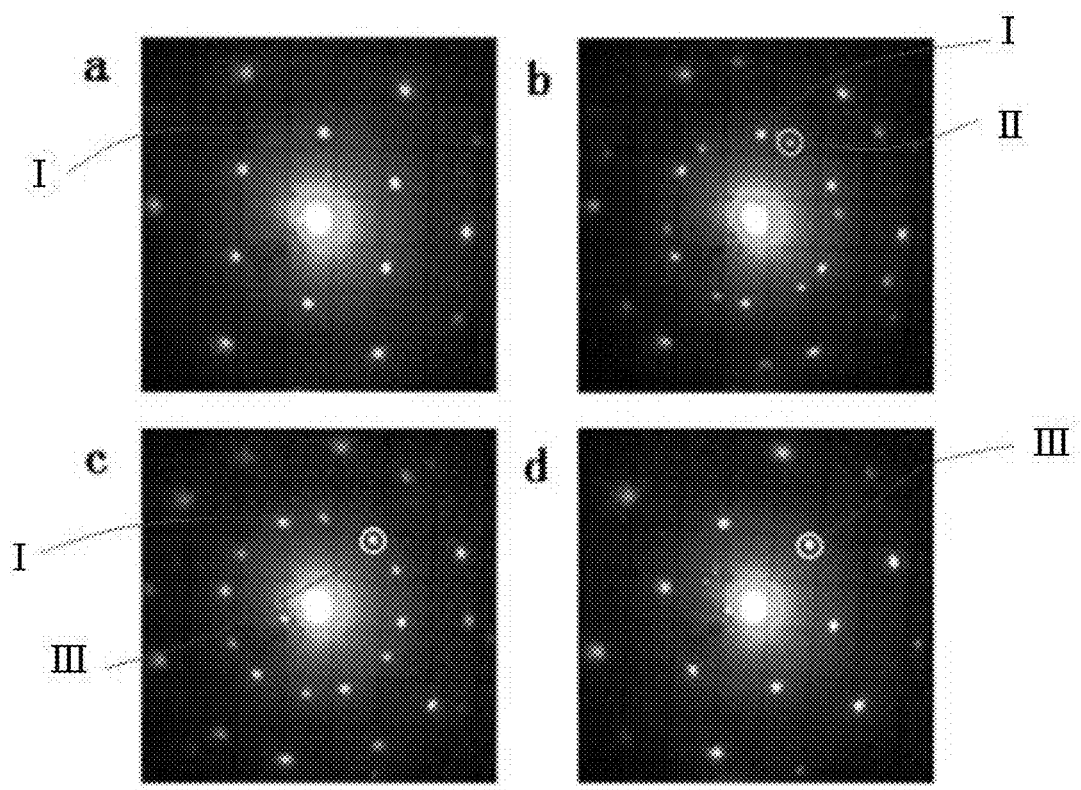
FIG. 9 shows electron diffraction patterns corresponding to four different regions in graphene island II of FIG. 5.

Since electrons passing through different graphene domains will be diffracted by different azimuthal angles, the diffraction image is a superposition of diffraction patterns corresponding to each graphene domain. Thus, the graphene island II cannot be recognized from its diffraction image. When the electron beam is focused, the diffraction pattern like selected area electron diffraction pattern can be achieved for both graphene island I and graphene island II. FIG. 8 shows four diffraction patterns of four areas of the graphene island I. FIG. 9 shows four diffraction patterns of four areas of the graphene island II. The diffraction patterns of graphene island I in FIG. 8 show the same set of hexagonal diffraction spots, confirming that graphene island I is a single crystal. In contrast, the diffraction patterns of graphene island II show three set of hexagonal diffraction spots number as I, II and III in FIG. 9, indicating that graphene island II is composed of at least three single crystal graphene domains.

Example 2

Figure 10:
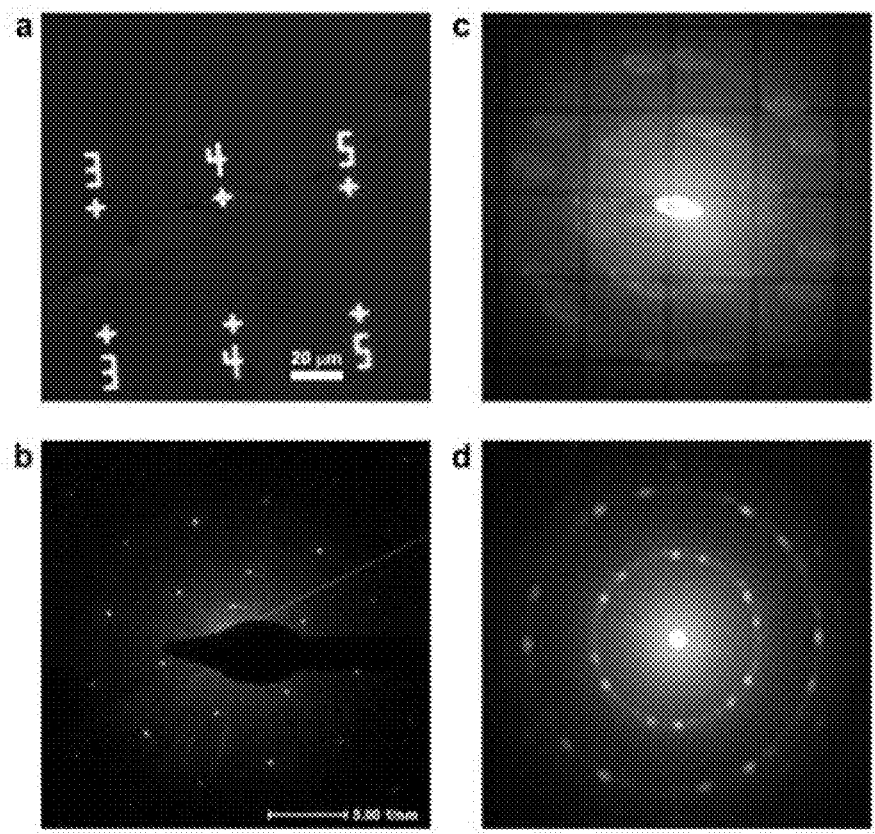
FIG. 10 shows transmitted electron diffraction and imaging of a large area continuous polycrystalline graphene of example 2.

Referring to FIG. 10a, in example 2, the two-dimensional nanomaterial sample 20 is a large area continuous polycrystalline graphene transferred onto a silicon substrate with a 300 nanometers $SiO_2$ layer. The optical contrast of graphene itself is homogeneous, indicating uniform single layer graphene with few double layer graphene islands. FIG. 10b shows the selected area electron diffraction pattern, confirming the graphene to be a single layer. The electron diffraction image is shown in FIG. 10c. Different from FIG. 6b, two sets of diffraction patterns with the same shape as the transmission spot appear in FIG. 10c. When the electron beam is focused, the diffraction pattern composed of two sets of hexagonal diffraction spots can be obtained, as shown in FIG. 10d. Since the graphene sample was verified to be single layer via optical of FIG. 10a, it is believed that FIGS. 10c and 10d reveal the crystal distribution of the whole graphene of millimeter size. Because the graphene is polycrystalline graphene composed of small single crystal graphene domains of micrometer size, the diffraction pattern of $mm^2$ polycrystalline graphene is a superposition of thousands of small graphene domains. Two sets of diffraction patterns indicate that the graphene has two preferred crystal orientations.

Example 3

Figure 11:
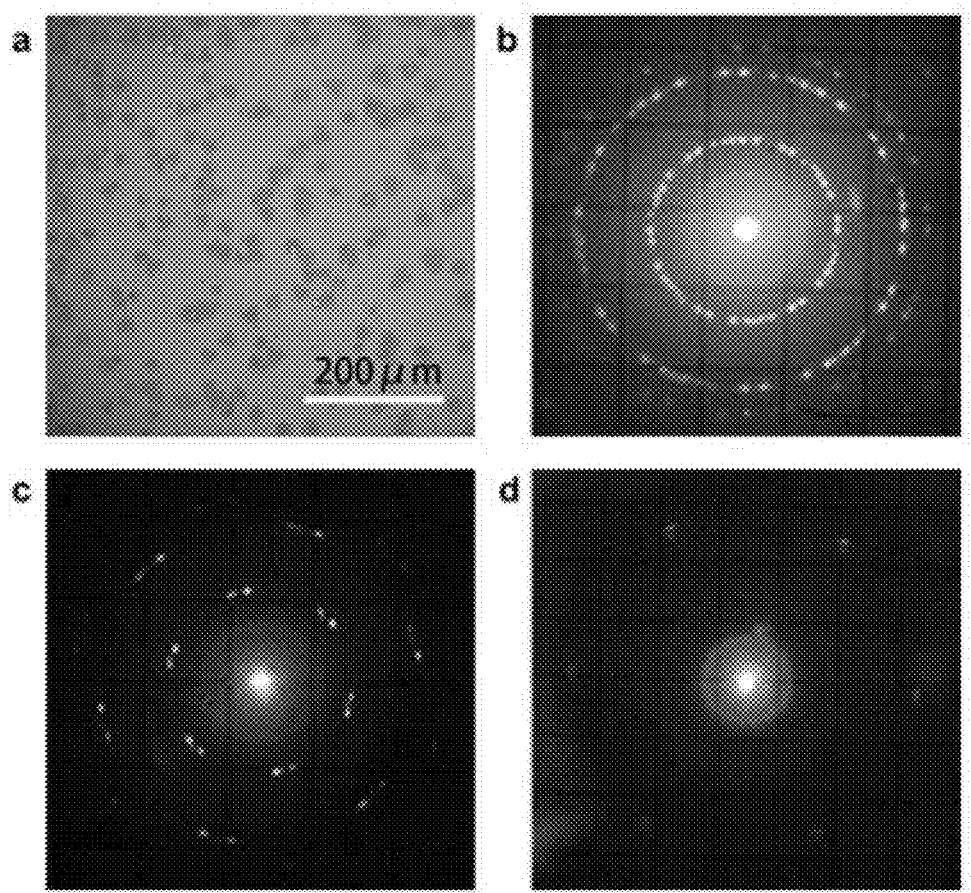
FIG. 11 shows transmitted electron diffraction and imaging of $MoS_2$ of example 3.

Referring to FIG. 11a, in example 3, the two-dimensional nanomaterial sample 20 is $MoS_2$ synthesized on a silicon substrate with oxidation layer. The darker flakes in FIG. 11a are $MoS_2$ with 19% coverage rate. The diffraction pattern as shown in FIG. 11b indicates that the $MoS_2$ flakes are polycrystalline. Many sets of diffraction spots come out in the image, showing none preferred orientation. However, when the electron beam covers few $MoS_2$ flakes, the orientations of these $MoS_2$ flakes can be clearly seen. FIG. 11c shows the transmitted electron diffraction pattern of $MoS_2$ with two crystal orientations, and FIG. 11d shows the transmitted electron diffraction pattern of $MoS_2$ with only one crystal orientation. The size of single $MoS_2$ flake is about tens of micrometers and much smaller than the beam size. Thus, the resolution of our low energy electron transmission diffraction can exceed its beam size limit of the transmission-type electron microscopy 10.

Example 4

Figure 12:
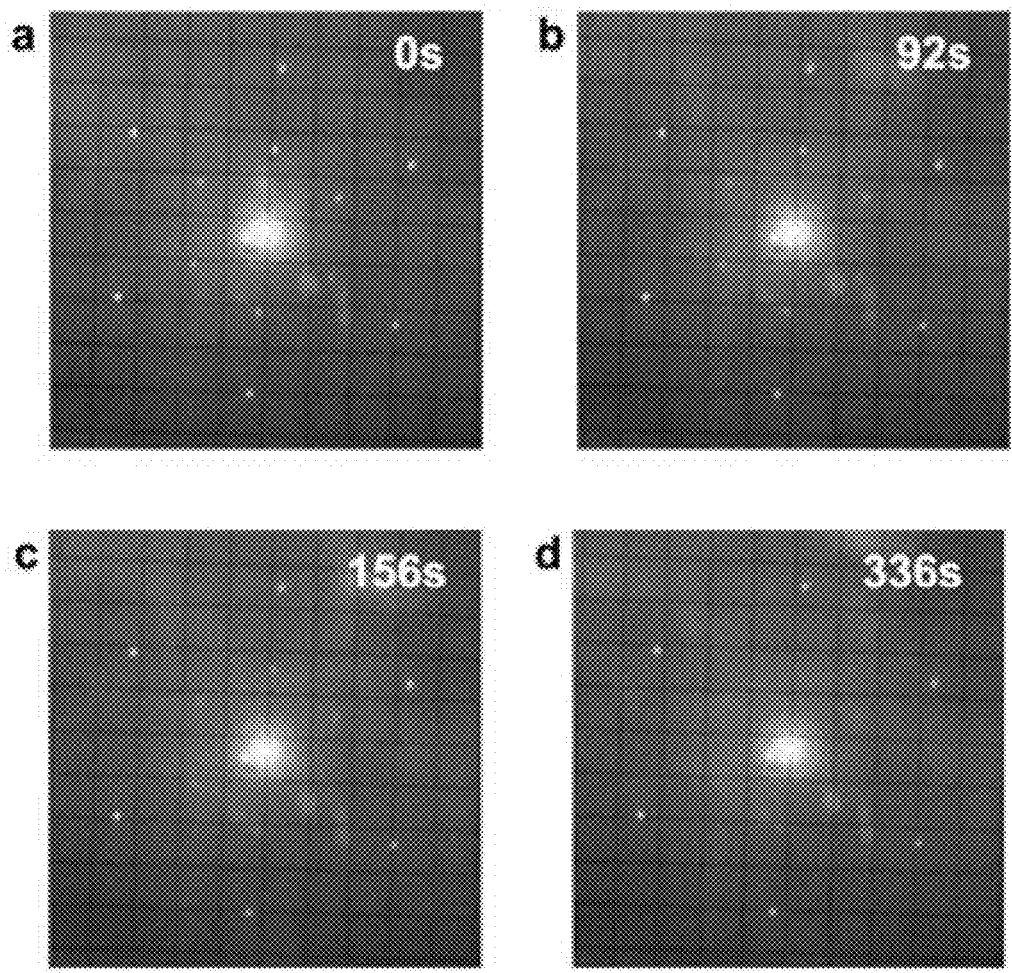
FIG. 12 shows transmitted electron diffraction pattern of water molecular adsorbed on a single crystal graphene of example 4 from appearing to disappearing, wherein exposure time was fixed at 15 s for each image.

The two-dimensional nanomaterial sample 20 of example 4 is the same as the single crystal graphene of the example 1. In example 4, the single crystal graphene is washed by deionized water before observation on the transmission-type electron microscopy 10. FIG. 12a shows that a set of hexagonal diffraction spots appeared near to the transmission spot as shown. The rotation angle of these diffraction spots was the same as {10-10} diffraction spots of graphene. However, after a few seconds, these extra diffraction spots gradually disappeared as shown in FIGS. 12b, 12c, and 12d. When the electron gun is moved to a new position, the same diffraction pattern could appear and disappear again. The extra diffraction spots should correspond to some metastable phenomena. Adsorption/desorption is one of the most possible cause for this phenomenon. When the CGF is heated to incandescence in a vacuum, and it is found that no extra diffraction spots existed. Since the CGF was rinsed in deionized water in preparation, it is assumed that water molecule was the most possible adsorption species. For the CGF sample after electron irradiation or being heated, water mist has been sprayed on the sample for two minutes. Then the extra diffraction pattern corresponding to the same region appeared again. As well as before, this diffraction pattern disappeared due to electron irradiation. Based on the contrast experiment above, it is believed that the extra pattern is caused by the adsorption of water molecules on graphene. The in-plane lattice spacing of this adsorption crystal lattice was calculated to be twice the {10-10} in-plane lattice spacing of graphene, and the crystal orientation of the adsorption crystal lattice was the same as graphene. It is called 2×2 0° adsorption pattern. Beyond the adsorption diffraction spots, adsorption diffraction image is also obtained when electron beam was enlarged. The adsorption image shows the same shape and rotation angle of the diffraction image of graphene, indicating that the adsorbed water molecules are highly correlated with the graphene lattice on a large scale. Besides single crystal graphene, the diffraction pattern of adsorption water can also be seen in polycrystalline graphene.

Example 5

Figure 13:
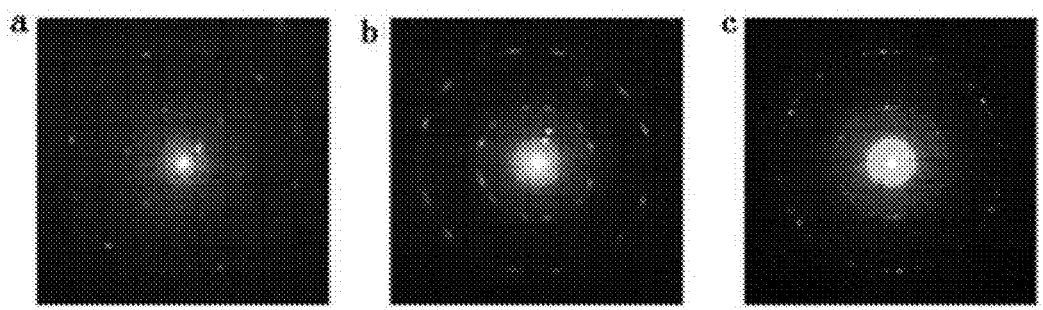
FIG. 13 shows transmitted electron diffraction patterns of water molecular adsorbed on a polycrystalline graphene of example 5 with different crystal orientations.

The two-dimensional nanomaterial sample 20 of example 4 is the same as the polycrystalline graphene of example 1. In example 5, the polycrystalline graphene is washed by deionized water before observation on the transmission-type electron microscopy 10. FIGS. 13a, 13b, and 13c show that the adsorption patterns of polycrystalline graphene with one, two, and three main crystal orientations, respectively. It is found that FIG. 13a has only one main crystal orientation, FIG. 13b has two main crystal orientations, and FIG. 13c has three main crystal orientations. In each of them, the rotation angle of adsorption diffraction spots varies along with the crystal orientation of graphene.

Example 6

Figure 14:
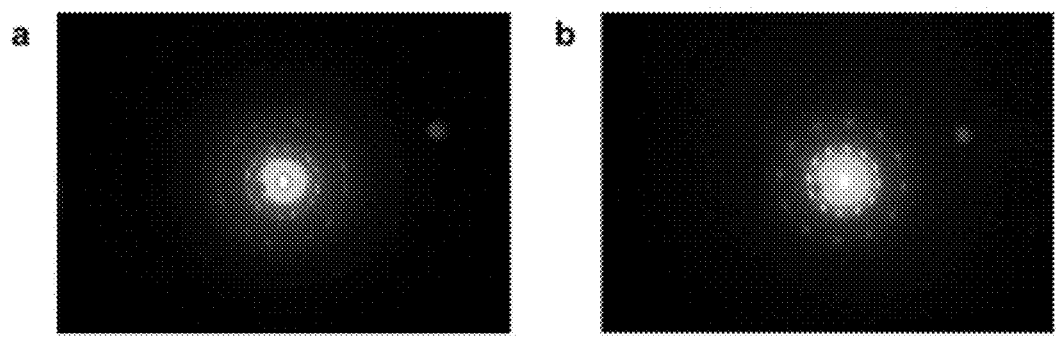
FIG. 14 shows transmitted electron diffraction patterns of a polycrystalline graphene of example 6.

The two-dimensional nanomaterial sample 20 of example 6 is the same as the large area continuous polycrystalline graphene of example 2. In example 5, the large area continuous polycrystalline graphene is transferred to two super-aligned drawn carbon nanotube films to form a CGF. FIGS. 14a and 14b are diffraction patterns of the same region of polycrystalline graphene, wherein FIG. 14a is obtained before rotating the polycrystalline graphene, and FIG. 14b is obtained after the polycrystalline graphene is rotated 90°. The sample in FIG. 14b was rotated 90°, relative to FIG. 14a. FIGS. 14a and 14b show that when the CGF sample was rotated 90°, the diffraction pattern of polycrystalline graphene is rotated 90°.

Example 7

Figure 15:
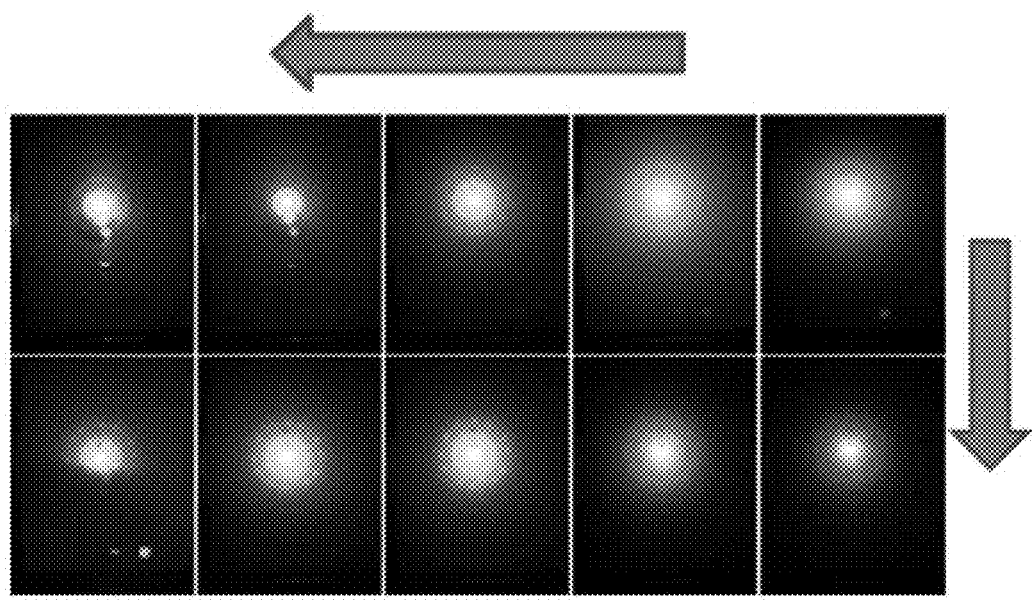
FIG. 15 shows a series of diffraction images obtained by moving the electron gun radiated on the CGF sample of example 7, wherein the arrows indicate the scanning directions, up and down first and then right to left.

The two-dimensional nanomaterial sample 20 of example 7 is the same as the large area continuous polycrystalline graphene of example 6. In example 7, 1 millimeter narrow slit was made by laser etching on the CGF sample before observation on the transmission-type electron microscopy 10. When the electron gun is moved, a series of diffraction images as shown in FIG. 15 are obtained. When the electron beam passed through the narrow slit, diffraction spots became dim and disappeared, indicating that the diffraction spots arise from the CGF sample.

Example 8

Figure 16:
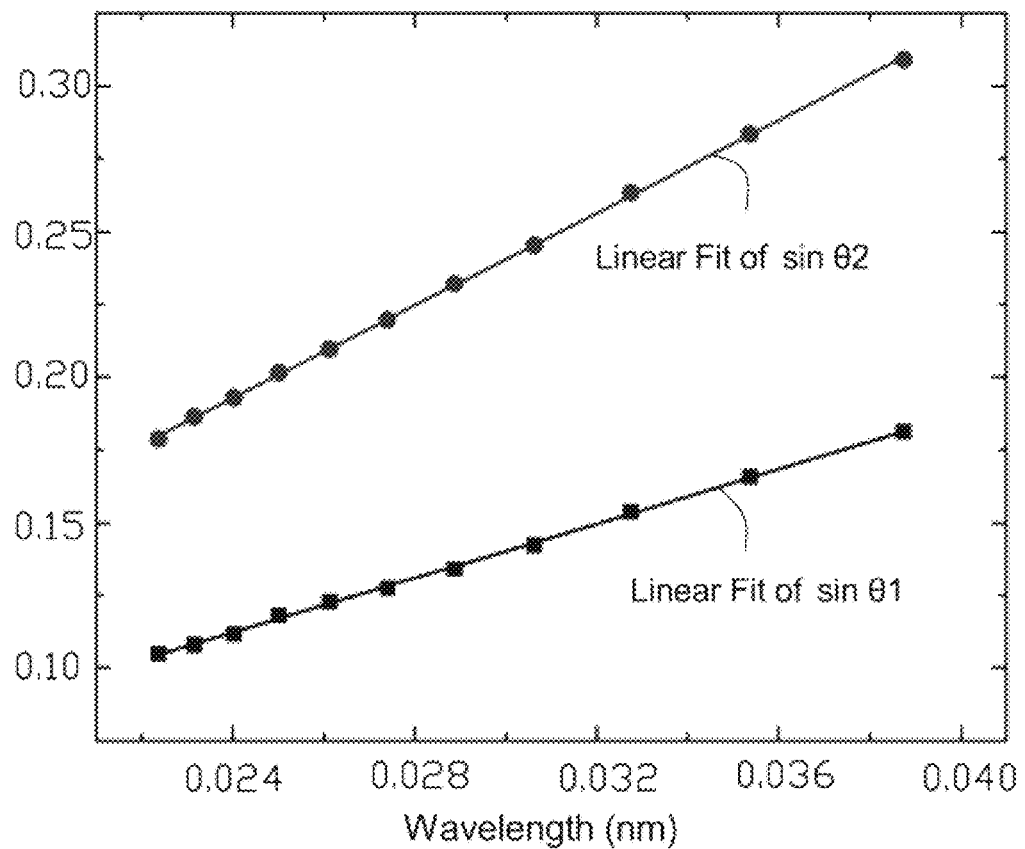
FIG. 16 shows $\sin \theta$ as a function of the wavelength of accelerated electrons, wherein $\theta 1$ is the diffraction angle corresponding to the graphene crystal face (10-10), and $\theta 2$ is the diffraction angle corresponding to the graphene crystal face (11-20).

The two-dimensional nanomaterial sample 20 of example 8 is the same as the single crystal graphene of example 1. In example 8, the single crystal graphene is transferred to super-aligned drawn carbon nanotube films to form a CGF. When the acceleration voltage is changed, the distance from the diffraction spots and rings to the transmission spot will change. If the camera length and the distance are measured from the transmission spot to the diffraction spot, the diffraction angle $\theta$ can be calculated. According to the theory of De Broglie, the wavelength of the accelerated electrons can be calculated. By doing that $\sin\theta$ versus the wavelength of the electrons $\lambda$ is plotted as the acceleration voltage changed in FIG. 16. $\theta1$ is the diffraction angle corresponding to the graphene crystal face (10-10), and $\theta2$ is the diffraction angle corresponding to the graphene crystal face (11-20). Then the corresponding in-plane lattice spacing of (10-10) face and (11-20) face is calculated by linear fitting the data according to formula $d \sin\theta = \lambda$. The in-plane lattice spacing d1 corresponding to (10-10) face was calculated to be 0.213 nanometers, and the in-plane lattice spacing d2 corresponding to (11-20) face was calculated to be 0.126 nanometers according to the formula $d=\lambda/\sin\theta$. Compared with the theoretical values of the in-plane lattice spacings of graphene, our experiment values are acceptable. As well as graphene, the in-plane lattice spacing of $MoS_2$ can also be calculated through this method.

It is to be understood that the above-described embodiments are intended to illustrate rather than limit the disclosure. Any elements described in accordance with any embodiments is understood that they can be used in addition or substituted in other embodiments. Embodiments can also be used together. Variations may be made to the embodiments without departing from the spirit of the disclosure. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A method for characterizing a two-dimensional nanomaterial sample, the method comprising:
   placing a two-dimensional nanomaterial sample in a vacuum chamber;
   radiating the two-dimensional nanomaterial sample by an incident electron beam, wherein the incident electron beam passes through the two-dimensional nanomaterial sample to form a diffraction electron beam and a transmission electron beam to form an image on an imaging device, wherein the image comprises a diffraction ring;
   obtaining an angle $\theta$ between the diffraction electron beam and the transmission electron beam, wherein the angle $\theta$ is calculated by a formula $\tan\theta=R/D$, R is a radius of the diffraction ring, and D is a distance between the two-dimensional nanomaterial sample and the imaging device; and
   calculating a lattice period d of the two-dimensional nanomaterial sample according to a formula $d \sin\theta \cong d\theta = \lambda$, wherein $\lambda$ represents a wavelength of the incident electron beam.

2. The method of claim 1, wherein the placing the two-dimensional nanomaterial sample in the vacuum chamber comprises locating the two-dimensional nanomaterial sample on a drawn carbon nanotube film to form a composite and fixing the composite on a sample holder in the vacuum chamber.

3. The method of claim 1, wherein the incident electron beam is larger than the two-dimensional nanomaterial sample, and the radiating the two-dimensional nanomaterial sample is performed by irradiating entire surface of the two-dimensional nanomaterial sample by the incident electron beam.

4. The method of claim 1, wherein the incident electron beam is smaller than the two-dimensional nanomaterial sample, and the radiating the two-dimensional nanomaterial sample is performed by irradiating partial surface or scanning entire surface of the two-dimensional nanomaterial sample by the incident electron beam.

5. The method of claim 1, wherein the image further comprises a transmission spot.

6. The method of claim 1, wherein the radius of the diffraction ring is obtained by processing the diffraction ring by a computer.

7. The method of claim 6, wherein the imaging device is a charge coupled device and connected to the computer.

8. The method of claim 1, wherein the imaging device is a fluorescent screen.

9. The method of claim 1, wherein the incident electron beam has an energy in a range from about 800 eV to about 3000 eV, a current in a range from about 0.1 microamperes to about 1 microampere, and a spot diameter in a range from about 100 micrometers to about 1 centimeter.

10. The method of claim 1, further comprising spraying other materials to the two-dimensional nanomaterial sample.

11. The method of claim 1, further comprising heating the two-dimensional nanomaterial sample.

12. A method for characterizing a two-dimensional nanomaterial sample, the method comprising:
placing a two-dimensional nanomaterial sample in a vacuum chamber; and
radiating the two-dimensional nanomaterial sample by an incident electron beam, wherein the incident electron beam passes through the two-dimensional nanomaterial sample to form a diffraction electron beam and a transmission electron beam to form an image on an imaging device; wherein the incident electron beam has an energy in a range from about 800 eV to about 3000 eV, a current in a range from about 0.1 microamperes to about 1 microampere, and a spot diameter in a range from about 100 micrometers to about 1 centimeter.

13. The method of claim 12, wherein the incident electron beam is larger than the two-dimensional nanomaterial sample, and the radiating the two-dimensional nanomaterial sample is performed by irradiating entire surface of the two-dimensional nanomaterial sample by the incident electron beam.

14. The method of claim 12, wherein the incident electron beam is smaller than the two-dimensional nanomaterial sample, and the radiating the two-dimensional nanomaterial sample is performed by irradiating partial surface or scanning entire surface of the two-dimensional nanomaterial sample by the incident electron beam.

15. The method of claim 12, wherein the image comprises a diffraction ring.

16. The method of claim 12, wherein the image comprises a transmission spot.

17. A method for characterizing a two-dimensional nanomaterial sample, the method comprising:
placing a two-dimensional nanomaterial sample in a vacuum chamber, wherein the placing the two-dimensional nanomaterial sample in the vacuum chamber comprises locating the two-dimensional nanomaterial sample on a drawn carbon nanotube film to form a composite and fixing the composite on a sample holder in the vacuum chamber;
radiating the two-dimensional nanomaterial sample by an incident electron beam, wherein the incident electron beam passes through the two-dimensional nanomaterial sample to form a diffraction electron beam and a transmission electron beam to form an image on an imaging device;
obtaining an angle $\theta$ between the diffraction electron beam and the transmission electron beam; and
calculating a lattice period d of the two-dimensional nanomaterial sample according to a formula $d \sin\theta \cong d\theta = \lambda$, wherein $\lambda$ represents a wavelength of the incident electron beam.

18. The method of claim 17, wherein the drawn carbon nanotube film comprises a plurality of carbon nanotubes orderly arranged and spaced from each other.

19. The method of claim 18, wherein the two-dimensional nanomaterial sample is located on two cross-stacking drawn carbon nanotube films.

* * * * *